(12) United States Patent
Vanderby et al.

(10) Patent No.: US 8,332,166 B2
(45) Date of Patent: Dec. 11, 2012

(54) METHOD AND APPARATUS USING LATERAL ACCESS TO OBTAIN ACOUSTOELASTIC EXTRACTION OF AXIAL MATERIAL PROPERTIES

(76) Inventors: Ray Vanderby, Madison, WI (US);
Hirohito Kobayashi, Madison, WI (US)

( * ) Notice: Subject to any disclaimer, the term of this patent is extended or adjusted under 35 U.S.C. 154(b) by 287 days.

(21) Appl. No.: 12/774,387

(22) Filed: May 5, 2010

(65) Prior Publication Data

US 2011/0276282 A1  Nov. 10, 2011

(51) Int. Cl.
*G06F 19/00* (2006.01)
*A61B 8/00* (2006.01)

(52) U.S. Cl. .......................... 702/42; 600/438

(58) Field of Classification Search ............... 702/42, 702/56; 600/438, 437
See application file for complete search history.

(56) References Cited

U.S. PATENT DOCUMENTS

| 7,744,535 B2 * | 6/2010 | Vanderby et al. ............ 600/438 |
| 2006/0025682 A1 | 2/2006 | Vanderby et al. |
| 2007/0089530 A1 | 4/2007 | Vanderby et al. |

\* cited by examiner

*Primary Examiner* — Bryan Bui (57) ABSTRACT

An ultrasound machine processes ultrasonic data according to acoustoelastic properties of the materials to obtain strain information without specific assumptions with respect to the material properties of the measured material or a variety of different material properties normally not obtained by ultrasound machines.

20 Claims, 4 Drawing Sheets

METHOD AND APPARATUS USING LATERAL ACCESS TO OBTAIN ACOUSTOELASTIC EXTRACTION OF AXIAL MATERIAL PROPERTIES

STATEMENT REGARDING FEDERALLY-SPONSORED RESEARCH OR DEVELOPMENT

This invention was made with United States government support awarded by the following agency:
NIH AR049266
The United States government has certain rights in this invention.

CROSS-REFERENCE TO RELATED APPLICATIONS

BACKGROUND OF THE INVENTION

The present invention relates to ultrasonic quantitative measurements and, in particular, to an improved apparatus and method for making ultrasonic measurements in axial material properties when only lateral access to the material is possible.

Conventional ultrasonic imaging provides a mapping of ultrasonic echo signals onto an image plane where the intensity of the echo, caused principally by relatively small differences in material properties between adjacent material types, is mapped to brightness of pixels on the image plane. While such images serve to distinguish rough structure within the body, they provide limited insight into the physical properties of the imaged materials.

Ultrasound "elastography" may be used to produce data and images revealing material properties such as strain under an externally applied stress, Poisson's ratio, Young's modulus, and other common strain and strain-related measurements. Quasi-static elastography provides these measurements by taking two images of a material in two different states of compression, for example no compression and a given positive compression. The material may be compressed by a probe (including the transducer itself) or, for biological materials, by muscular action or movement of adjacent organs. Strain may be deduced from these two images by computing gradients of the relative shift of the material in the two images along the compression axis. Quasi-static elastography is analogous to a physician's palpation of tissue in which the physician determines stiffness by pressing the material and detecting the amount of material yield (strain) under this pressure.

Ultrasound "acoustoelasticity" provides an alternative method of computing material properties using a mathematical description of the relationships between sound propagation and material properties to deduce the properties more directly. For example, a measurement of reflected energy as ultrasound passes through a front and rear boundary of a material in tension can be used to deduce the strain of the material along the axis of tension and the stiffness of the material along the direction of ultrasound propagation. This technique, pioneered by the present inventors, is described in U.S. patent application 2007/0089530 filed Oct. 16, 2006 and hereby incorporated by reference.

The measurement of loads (stress) and stiffness in axial direction can be important in medicine, for example, in the assessment of disease or repair of ligaments and tendons. While the above described acoustoelastic technique allows the determination of axial strain (e.g. stretching along the length of the tendon) it does not measure the axial stress (e.g. tension along the length of the tendon) or axial material properties such as stiffness which may, particularly in tendons and ligaments, vary substantially between the axial and transverse directions.

While it is generally possible to measure axial properties simply by shifting the direction of the transducers to be aligned along the axis of measurement, this is not practical with in situ tendon and ligaments. Many important applications where measurement of axial properties of tendons and ligaments is desired, occur when the tendons and ligaments are under tension in the body and only lateral access to the tendon or ligament is available, for example, through thin overlying tissue or a surgical incision.

BRIEF SUMMARY OF THE INVENTION

The present inventors have developed a new apparatus and technique that can provide axial properties of the material when only lateral access is available for the ultrasound probes. Generally, the device provides a transverse directed ultrasonic transducer that determines transverse properties using the acoustoelastic techniques described above. A pair of angled transducers then provides an angled measurement of both transverse and axial properties. Mathematical combination of these two measurements can extract isolated axial properties.

Specifically then, the present invention provides an ultrasound system for measuring axial material properties of material using ultrasound. The system includes an ultrasound transducer assembly transmitting an ultrasound signal into the material along a first transverse direction and receiving the ultrasound signal after reflection and modification by the material with a first and second tension applied along the axial extent of the material. In addition, the ultrasound transducer may transmit an ultrasound signal into the material along a first oblique direction at an angle between the transverse direction and the axial extent of the material and receive the ultrasound signal after reflection and modification by the material at the first and second tension. A processor receives and processes these signals along the transverse and angle directions according to a stored program to determine at least one of axial stress and axial stiffness of the material.

It is thus one feature of at least one embodiment of the present invention to provide a measurement of axial properties of the material when only lateral access to the material can be obtained.

The processor may determine transverse material properties from the ultrasonic signal along the transverse direction and may determine axial properties from the transverse properties by analysis of the time of flight of the ultrasound along the transverse and angle directions and the known geometry of the path of the ultrasound along the transverse and oblique direction.

It is thus one feature of at least one embodiment of the present invention to deduce axial properties from transverse properties and a combination of transverse and axial time of flight of the ultrasonic signal.

The processor may determine the transverse material properties from a time of flight of ultrasound between the first and second material positions and a reflection coefficient indicating reflected ultrasonic energy at the first and second material positions. The reflection coefficient may be a measure of a relative power reflected at the material positions in a predetermined frequency range.

It is thus one feature of at least one embodiment of the present invention to make use of acoustoelastic analysis to determine the transverse properties of the material.

The ultrasonic transducer assembly may include three ultrasonic transducers fitting within a housing having surfaces to align the housing with respect to an axial direction of the material wherein the first ultrasonic transducer directs ultrasonic energy substantially perpendicular to the tissue when the housing is aligned with the tissue and the second and third ultrasonic transducers direct energy at complementary obtuse and acute angles with respect to a perpendicular to the tissue when the housing is aligned with the tissue.

It is thus one feature of at least one embodiment of the present invention to provide a simple apparatus for rapid determination of axial material properties, for example, in a surgical setting.

The oblique direction is at an angle that is smaller than "critical angle" that will result in surface wave.

It is thus one feature of at least one embodiment of the present invention to minimize interference resulting from a surface wave in the transverse direction.

The ultrasound system may be surrounded by a transmission material and the first and second material positions are interfaces between the material and the transmission material. The interface material may be tissue or maybe a coupling elastomer of known material properties.

It is thus one feature of at least one embodiment of the present invention to provide a system that may be used with ligaments and tendons surrounded by other tissue or isolated for measurement.

These particular objects and advantages may apply to only some embodiments falling within the claims, and thus do not define the scope of the invention.

DETAILED DESCRIPTION OF THE PREFERRED EMBODIMENT

Figure 1:
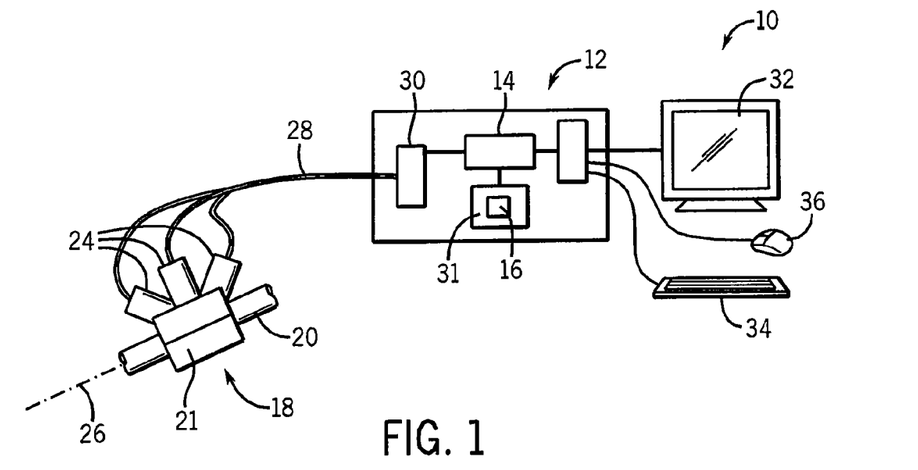
FIG. 1 is a simplified block diagram of an ultrasound scanner suitable for use with the present invention having a transducer system providing simultaneous transverse and oblique ultrasonic measurements.

Referring now to FIG. 1, an acoustoelastographic ultrasound system 10 suitable for use with the present invention may employ an ultrasonic imaging machine 12 providing the necessary hardware and/or software to collect and process ultrasonic echo signals using a processor 14 executing a stored program 16 held within the ultrasonic imaging machine 12.

An ultrasonic transducer assembly 18 associated with the ultrasonic imaging machine 12 may have a housing 21 positionable about a ligament or tendon 20 extending an axial direction 26. The ultrasonic transducer assembly 18 may include, in one embodiment, three ultrasonic transducers 24 in the housing to direct one ultrasonic beam generally perpendicular to the axial direction 26 of the tendon 20 and to project and receive a second ultrasonic beam at any angle that is smaller than "critical angle" (e.g., an angle above which the ultrasound passes predominately in a surface wave perpendicular to the to the axial direction 26. Generally angle of 45° to the axial direction can be used.

The echo signals from these beams may be received at the ultrasonic transducer assembly 18 to be converted to an electrical echo signal.

Multiple acquisitions of echo signals may be obtained with the ligament 20 in different states of tension, for example, by muscular activity or by mechanical gripping of the tendon or similar technique.

The electrical echo signals may be communicated along lead 28 to interface circuitry 30 of the ultrasonic imaging machine 12. The interface circuitry 30 provides amplification, digitization, and other signal processing of the electrical signal as is understood in the art of ultrasonic imaging. The digitized echo signals are then transmitted to a memory 31 for storage (along with program 16) and subsequent processing by a processor 14, as will be described below.

After processing, the echo signals may be used to construct an image displayed on graphical display 32 and axial material properties may be displayed quantitatively on the graphical display 32 as well as conventional B-mode images. Input commands affecting the display of the echo signals and their processing may be received via a keyboard or cursor control device 34, such as a mouse, attached to the processor 33 via interface circuitry 30, as is well understood in the art.

Figure 2:
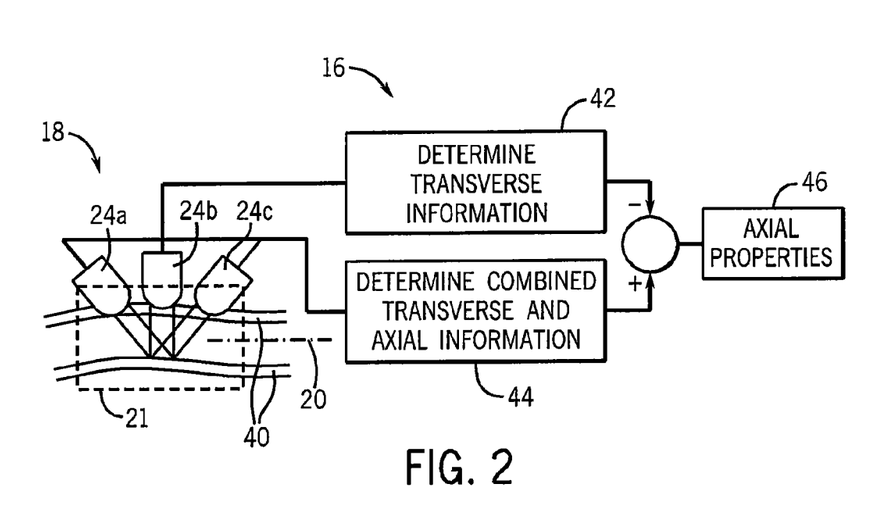
FIG. 2 is a simplified block diagram of a combination of signals from the two transducer directions to provide for axial measurements.

Referring now to FIG. 2, as noted above, a center transducer 24b of the ultrasonic transducer assembly 18 may be positioned within the housing 21 to direct a first beam perpendicularly to the axial direction 26. This first beam passes through an outer transmissive material 40 into the tendon 20 through an interface between the two that causes a first reflection of ultrasonic energy back to the transducer 24b. The wave continues until it strikes an interface between the tendon 20 and outer transmissive material 40 on the opposite side of the tendon 20 which also produces an echo reflecting altered sonic energy back to the transducer 24b. The outer transmissive material 40 may be other tissue surrounding the tendon 20 or maybe compliant elastomeric pads when the apparatus is used surgically. In general, the signals from these echoes are processed to determine transverse properties of the tendon along an axis perpendicular to the axial direction 26. Specifically these transfers properties as will be described below include a transverse stiffness value $C_{33}$ (where the 33 subscript indicates the transverse orientation) and a transverse strain value $e_{33}$ occurring between the two tensions applied to the tendon, as well as a transverse velocity value $V_{33}$ and a transverse time of flight $T_{33}$ being the time that it takes for the ultrasonic energy to pass between the two interfaces between outer transmissive material 40 and ligament 20. The determination of these values will be described below and is indicated generally by process block 42.

Housing 21 also holds transducers 24a and 24c that flank transducer 24b and are tipped at approximate 45° true with respect to a normal to axial direction 26 to project a second ultrasonic beam from transducer 24a to be received by transducer 24c along this oblique path that has both transverse and axial dimensions. In this case at least a three echoes can be obtained from which it may deduce the time it takes the ultrasonic energy to cross into a ligament 20 from transducer 24a and to exit the ligament 20 proximate to transducer 24c after reflecting off the interface between outer transmissive material 40 and the ligament 20 opposite transducer 24b. This time information is extracted as indicated by process block 44 and includes both transverse and axial information. Of principal interest is the time of flight $T_{13}$ (where the subscript 13 indicates both axial and transverse components) within the tendon 20 along this geometric path.

In the present invention, information from process block 42 providing transverse material property may then be combined with the information from process block 44 providing transverse and axial information to produce axial information per process block 46 using a set of transducers that have only lateral access to the tendon 20, that is from the side and not from the ends of the tendon as would be required using normal ultrasonic analysis for axial properties.

Figure 3:
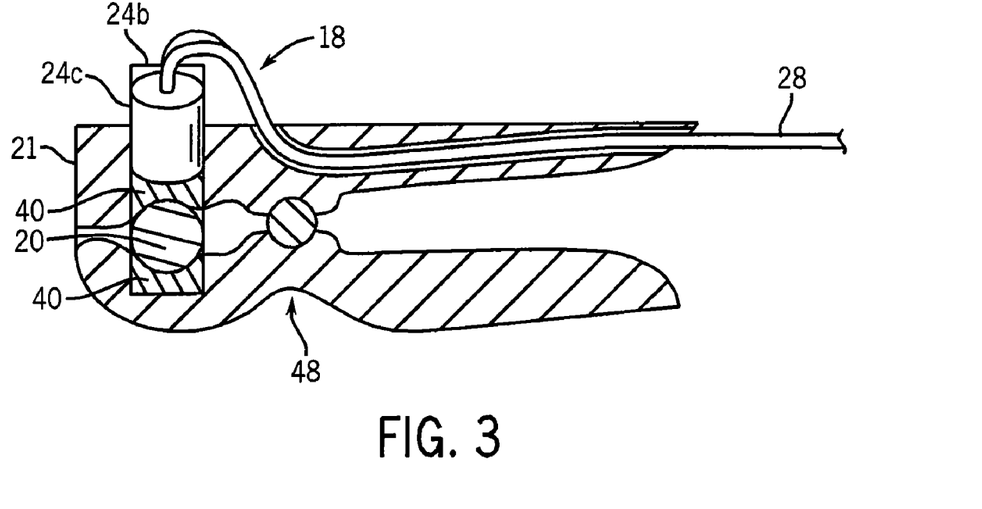
FIG. 3 is an elevational cross-section of a probe for providing the simultaneous ultrasonic measurements of FIG. 1.

Referring now to FIG. 3, in one embodiment it is envisioned that the housing 21 holding the ultrasonic transducer assembly 18 may provide a clamping mechanism 48 allowing the tendon 20 to be engaged, for example, by surgical opening and providing coupling outer transmissive material 40, for example, a compliant elastomer, to cushion and surround the tendon 20 and provide ultrasonic coupling from the transducers 24 to the tendon 20.

Obtaining Transverse Properties

Using Acoustoelastic Strain Gauge (ASG)

Figure 5:
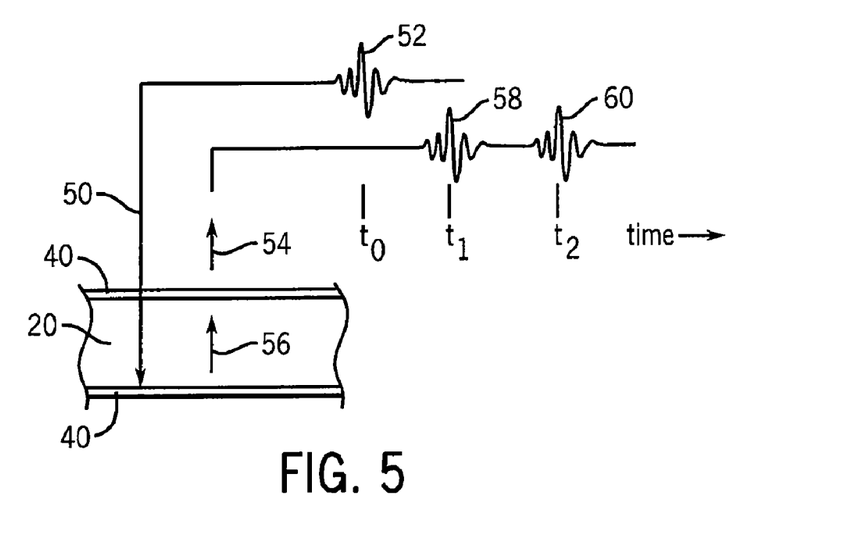
FIG. 5 is a simplified representation of the transverse measurements used by the present invention.
Figure 6:
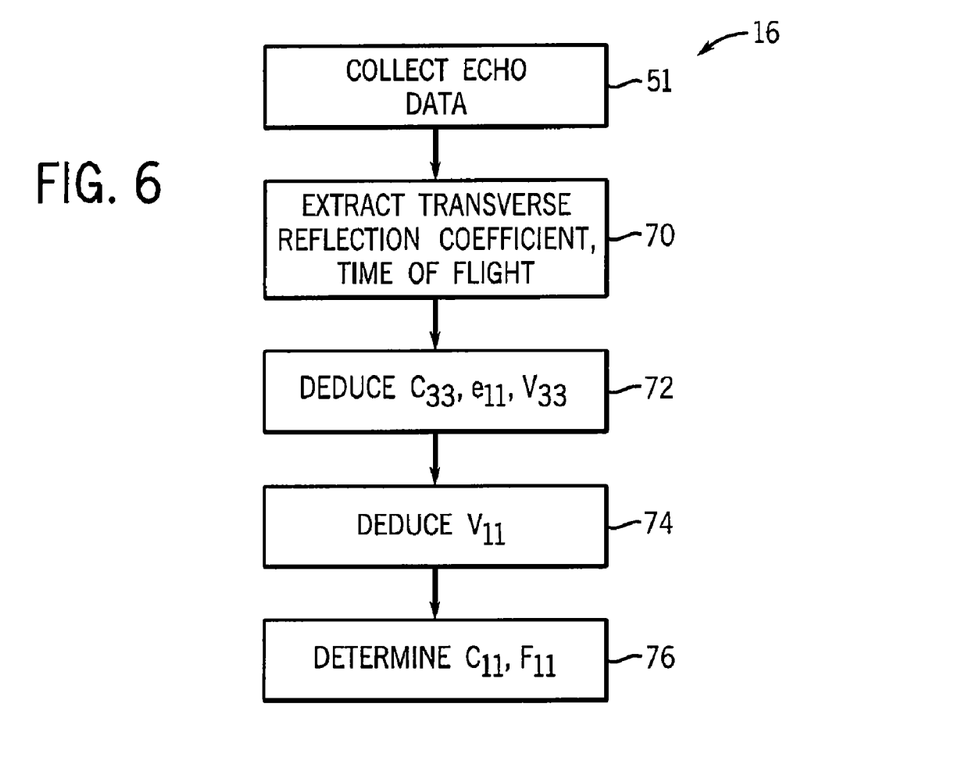
FIG. 6 is a flow chart of the steps of the present invention as executed by a processor following a stored program.

Referring to FIG. 6, the program 16 initially collects the echo data along the transverse and lateral axes as indicated by process block 51. Referring momentarily to FIG. 5, in the transverse direction transducer 24b will provide ultrasonic signal 50 directed transversely into the tendon 20 having a wave shape 52 at a first time $t_0$. This ultrasonic signal 50 will produce two echoes, echo 54 from a closest interface between outer transmissive material 40 and the tendon 20 and echo 56 from a furthest interface between the outer transmissive material 40 and the tendon 20. These echoes 54 and 56 will produce waveforms 58 and 60 at time $t_1$ and $t_2$ respectively.

Figure 4:
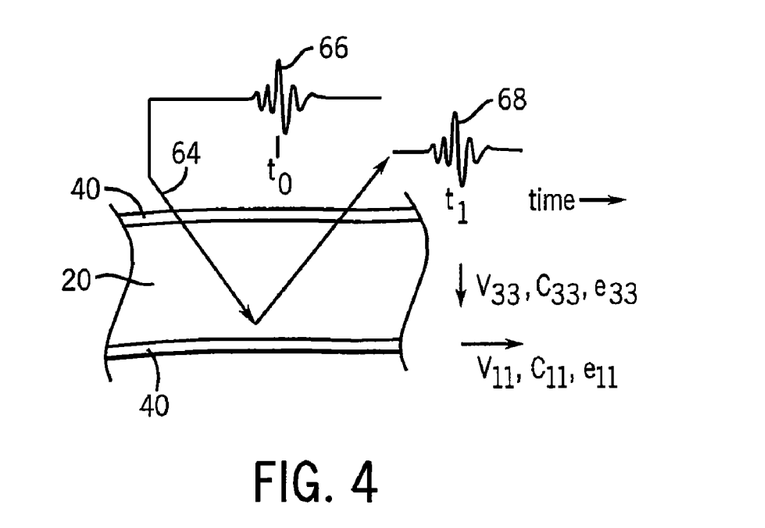
FIG. 4 is simplified representation of the tendon showing directions and variables used in the calculation of the present invention.

Referring now also to FIG. 4, the difference in time between $t_1$ and $t_2$, termed ($T_{0\_33}$) will be used to determine a transverse velocity $V_{33}$ as will be described below as well as transverse stiffness $C_{33}$ and transverse strain $e_{33}$ where the subscript 33 indicates the transverse direction.

Similarly, in the oblique direction transducer 24a will provide an angled ultrasonic signal 64 having a wave shape 66 at time $t_0$ that will be received by transducer 24c at time $t_1$ as wave shape 68. The difference between these two times $t_1$ and $t_2$, termed ($T_{0\_TOTAL}$) will be used to deduce the axial velocity $V_{11}$ as will be described below as well as axial stiffness $C_{11}$ and axial strain $e_{11}$ where the "11" subscript indicates the axial direction. The actual time for the ultrasonic signals to pass through the tendon 20, excluding the outer transmissive material 40, may be either assumed to be the total time when the regions of the outer transmissive material 40 are small or may be deduced by looking at multiple echoes that indicate the interface crossings.

Referring now to again to FIG. 6 at process block 70 the transverse information described with respect to FIG. 5 is used to extract time of flight and reflection coefficients for two states of tension of the ligament 20 as has previously been described with respect to the above referenced patent application 2007/0089530 now reproduced for completeness below.

Frequency Domain Analysis

Strain e presented in sections hereafter represents the axial strain $e_{11}$. Based on the assumption of tissue incompressibility (volume consistency through deformation), the strain in transverse (thickness) direction $e_{33}$ is related to axial strain $e=e_{11}$ by following relation.

$$e_{33} = \frac{1}{\sqrt{1+e_{11}}} = \frac{1}{\sqrt{1+e}} \tag{0}$$

In addition, all material properties in all directions (axial and transverse) are treated as function of axial strain e.

First, the transverse stiffness (e.g., along the transverse axis) is assumed to be some function of the applied axial strain e, for example, a general second order function such as:

$$\tilde{C}_{33}(e) \approx c_2 \cdot e^2 + c_1 \cdot e + C_{33}. \tag{1}$$

As will be discussed later, the order or the form of this function is not critical and is chosen so that it can be fit to the data. Further it is assumed that the tissue is nearly incompressible, that is, $e_{11}$ is a function of and can be deduced from $e_{33}$ and vice versa and so stiffness can be formulated with either axial or transverse strain as the dependent variable. This is true for other strain dependent phenomena, i.e. wave propagation velocity, wave travel time, and reflection coefficient which are defined below. From this point forward, it is assumed that all strain dependent phenomena are defined as a function of axial strain e with the subscripts dropped for simplicity.

Because of this assumption of near incompressibility (i.e. the material density does not depend on the amount of strain or deformation), it follows that:

$$\rho^S(e) \approx \rho^S(e=0) = \rho_0^S. \tag{2}$$

Under these assumptions, the wave velocity through thickness (in transverse direction) is given by:

$$V(e) = \sqrt{\frac{\tilde{C}_{33}(e)}{\rho^S(e)}} \approx \sqrt{\frac{\tilde{C}_{33}(e)}{\rho_0^S}}. \tag{3}$$

The reflection coefficient at the interface of surrounding medium (outer transmissive material 40) and target medium (e.g. ligament 20) is defined by:

$$R(e) = \frac{\rho^S V(e) - \rho^W V^W}{\rho^S V(e) + \rho^W V^W}$$

or re-organized form $$\rho^S \cdot V(e) = \frac{1+R(e)}{1-R(e)} \rho^W \cdot V^W. \tag{4}$$

In these relations, superscripts S and W respectively represent the target tissue 20 (solid) and the surrounding medium (e.g., water equivalent) or known elastomer of outer transmissive material 40.

Combining equations (1)-(4), a relation between material properties ($c_1$, $c_2$, $C_{33}$, $\rho_0$) and impedance square (right hand side of equation) for each stretched state is derived as:

$$\rho_0^S (c_2 \cdot e^2 + c_1 \cdot e + C_{33}) = \left[\frac{(1+R(e))}{(1-R(e))} \rho^W V^W\right]^2 = IPS(e). \quad (5)$$

When the material properties of the outer transmissive material 40 are known, the reflection coefficient can be retrieved from measured echo signals, and the impedance square parameter on the right hand side is known. As will be noted below, however, knowledge of the material properties of the surrounding material is not required.

Similarly, the relation between the material property and impedance square at non-stretched state can be derived as:

$$\rho_0^S C_{33} = \left[\frac{(1+R_0)}{(1-R_0)} \rho^W V^W\right]^2 = IPS_0. \quad (6)$$

By the taking the ratio of reflection information equations (5) and (6), the unknown target tissue density cancels and is eliminated as a parameter required to determine the other material properties. This is important because in-vivo tissue density is very difficult to measure.

$$\frac{\rho_0^S(e)\tilde{C}_{33}(e)}{\rho_0^S C_{33}} \approx \frac{c_2 \cdot e^2 + c_1 \cdot e}{C_{33}} + 1 = \quad (7)$$

$$\frac{\left[\frac{(1+R(e))}{(1-R(e))} \rho^W V^W\right]^2}{\left[\frac{(1+R_0)}{(1-R_0)} \rho^W V^W\right]^2} = \frac{\left[\frac{(1+R(e))}{(1-R(e))}\right]^2}{\left[\frac{(1+R_0)}{(1-R_0)}\right]^2} = \frac{IPS(e)}{IPS_0}$$

Here, the left hand side term represents the unknown normalized material property. Again, the right hand side is measured or known information. Since the material properties of the surrounding medium ($\rho^W V^W$) are cancelled out in the same process, the material properties of the surrounding medium that were originally assumed to be known are also not essential to the analysis.

Time Domain Analysis:

The travel time at $e=0$ (non-stretched state or lesser stretched state) can be related to the unloaded tissue thickness D and wave velocity $V_0$ by:

$$T_0 = \frac{2D}{V_0} = 2D\sqrt{\frac{\rho_0^S}{C_{33}}}. \quad (8)$$

Similarly, the travel time at $e \neq 0$ (stretched state or greater stretched state) is given by:

$$T(e) = \frac{2d(e)}{V(e)}. \quad (9)$$

Here, the wave velocity V and tissue thickness d at a stretched state are given by:

$$V \approx \sqrt{\frac{\tilde{C}_{33}(e)}{\rho_0^S}} = \sqrt{\frac{c_2 e^2 + c_1 e + C_{33}}{\rho_0^S}} \quad (10)$$

and $$d(e) = \frac{D}{\sqrt{1+e}}. \quad (11)$$

By taking the ratio of the wave travel time equations (10) and (11):

$$\left(\frac{T_0}{T(e)}\right)^2 = \left(\frac{2D/V_0}{2d/V}\right)^2 = \left(\sqrt{\frac{\tilde{C}_{33}(e)}{C_{33}}} \sqrt{1+e}\right)^2 = \frac{IPS(e)}{IPS_0}(1+e), \quad (12)$$

the strain $e = e_{11}$ applied to the tissue can be evaluated as:

$$e = \frac{IPS_0}{IPS(e)} \left(\frac{T_0}{T(e)}\right)^2 - 1. \quad (13)$$

Since the right hand side of this relation contains parameters that are measured directly from wave signals, the applied strain can be evaluated directly without any supplemental information. Once the applied strains are evaluated, they are used in equation (7) to compute the normalized stiffness:

$$\frac{c_2 \cdot e^2 + c_1 \cdot e}{C_{33}} + 1 = \frac{\left[\frac{(1+R(e))}{(1-R(e))}\right]^2}{\left[\frac{(1+R_0)}{(1-R_0)}\right]^2} = \frac{IPS(e)}{IPS_0}. \quad (7)$$

If the density of the target tissue $\rho_0^S$ is known prior to the testing, the coefficients in the transverse stiffness function can be directly evaluated by substituting the evaluated strain into relation (5):

$$c_2 \cdot e^2 + c_1 \cdot e + C_{33} = \frac{1}{\rho_0^S}\left[\frac{(1+R(e))}{(1-R(e))} \rho^W V^W\right]^2 = \frac{1}{\rho_0^S} IPS(e). \quad (5')$$

Once the transverse stiffness is given as a function of applied axial strain e, the tissue thickness at any strain level can be calculated from relation: (9)

$$d(e) = \frac{T(e)}{2} V(e) = \frac{T(e)}{2} \sqrt{\frac{c_2 \cdot e^2 + c_1 \cdot e + C_{33}}{\rho_0^S}}. \quad (14)$$

The result of these calculations is to determine the transverse stiffness $C_{33}$, and axial strain e (termed e in these equations) as indicated by process block 72 of FIG. 6.

Obtaining Axial Properties

Using Acoustoelastic Strain Gauge (ASG) Derived Values

Using these derived transfer properties, the axial properties can now be determined. In the present invention, as noted above, we have previously determined $e_1$ $$e = \frac{C_{33}}{\tilde{C}_{33}(e)}\left(\frac{T_{0\_33}}{T_{33}(e)}\right)^2 - 1 = \frac{\left[\frac{(1+R_{33}(e))}{(1-R_{33}(e))}\right]^2}{\left[\frac{(1+R_{0\_33})}{(1-R_{0\_33})}\right]^2}\left(\frac{T_{0\_33}}{T_{33}(e)}\right)^2 - 1 \quad (7)(13)$$

and we have previously determined normalized $C_{33}$ $$\frac{\tilde{C}_{33}(e)}{C_{33}} \approx \frac{c_2}{C_{33}} \cdot e^2 + \frac{c_1}{C_{33}} \cdot e + 1 = \frac{\left[\frac{(1+R_{33}(e))}{(1-R_{33}(e))}\right]^2}{\left[\frac{(1+R_{0\_33})}{(1-R_{0\_33})}\right]^2}. \quad (15)$$

This equation is a fundamental relationship in acoustoelastics:

$$\vec{V} = \vec{V}_{11} + \vec{V}_{33} = \sqrt{\frac{\tilde{C}_{11}(e) + t_{11}(e)}{\rho}}\vec{i} + \sqrt{\frac{\tilde{C}_{33}(e)}{\rho}}\vec{k}. \quad (16)$$

In equation 16, $t_{11}(e)$ is axial stress as a function of axial strain.

We don't know V directly because the geometry of the path may be affected by propagation velocity changes in the tissue and changes in stiffness according to the loading (the acoustoelastic effect) but we know normalized $V_{33}$ from perpendicular transducer and can deduce normalized $V_{11}$ as follows:

$$T_{0\_TOTAL}^2 = T_{0\_33}^2 + T_{0\_11}^2 \to T_{0\_11} = \sqrt{T_{0\_TOTAL}^2 - T_{0\_33}^2}, \quad (17)$$

$$T_{TOTAL}(e)^2 = T_{33}(e)^2 + T_{11}(e)^2 \to T_{11}(e) = \sqrt{T_{TOTAL}(e)^2 - T_{33}(e)^2} \quad (18)$$

and $$d_{11}(e) = D_{11} \cdot (1+e) \quad (19)$$

where the value of $T_{0\_TOTAL}$ and $T_{0\_33}$ is determined as described above. $D_{11}$ and $d_{11}(e)$ represent the axial length of a element of tissue under consideration at pre- and post-deformed states respectively.

This gives us normalized $V_{11}$, per process block 74, as follows:

$$e = \frac{V_{11}(e)}{V_{0\_11}}\frac{T_{11}(e)}{T_{0\_11}} - 1 \to \frac{V_{11}(e)}{V_{0\_11}} = (e+1)\frac{T_{0\_11}}{T_{11}(e)}. \quad (20)$$

Knowing $C_{33}$, e and $V_{11}$ and $V_{33}$ we can determine $C_{11} + t_{11}$ using equation (16). Separating axial stiffness and stress, $C_{11}$ and $t_{11}$ can be done for a linear material simply by knowing that $C_{11} \cdot e = t_{11}$. For a nonlinear material such as tendons it is necessary to integrate $C_{11}$ with respect to e to get $t_{11}$ as follows:

$$t_{11} = \int_e C_{11} de. \quad (21)$$

In practice this integral can be resolved by defining $C_{11}$ as a function of e in terms of a, b, and c used as parameters for the nonlinear function, for example, coefficients of a second order polynomial. Stress $t_{11}$ is also defined by the same parameters plus the constant of integration which will be zero. Accordingly, knowledge of a, b, and c. which can be determined by empirical analysis of tendons, will permit the calculation of stiffness $C_{11}$ as a function of strain and also calculate stress $t_{11}$ as a function of strain per process block 76. Stresses can be integrated over an area to compute axial force.

Figure 7A:
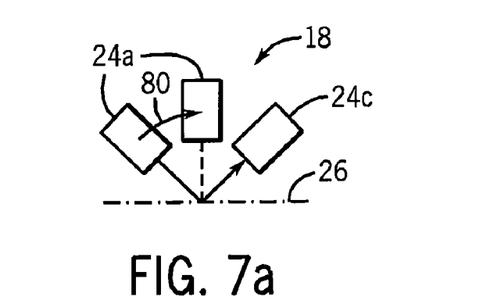
FIGS. 7a and 7b are diagrams showing alternative transducer designs.

Referring now to FIG. 7a in an alternative embodiment of the ultrasonic transducer assembly 18, a single ultrasonic transducer 24a may serve the role of both of transducers 24a and 24b described in FIG. 2. In this embodiment, transducer 24a is originally positioned at an angle less than the critical angle with respect to axial direction 26 for obtaining the oblique data and then pivoted as indicated by arrow 80 to a perpendicular direction to serve in the role of transducer 24b as described above.

These methods could be used for materials other than biological tissues. The ultrasonic signals processed can be raw ultrasound or processed B-mode data.

Figure 7B:
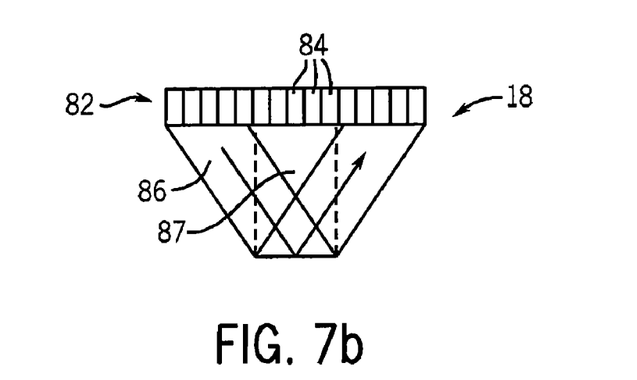

Alternatively, as shown in FIG. 7b, a phased array detector 82, providing for multiple transmitting and receiving elements 84, may be operated by appropriately phasing the transmit and receive signals among each of the elements 84 to direct a first beam 86 at an oblique angle and the second beam 87 at a perpendicular angle providing comparable data to that obtained by the ultrasonic transducer assembly 18 of FIG. 2.

Figure 8:
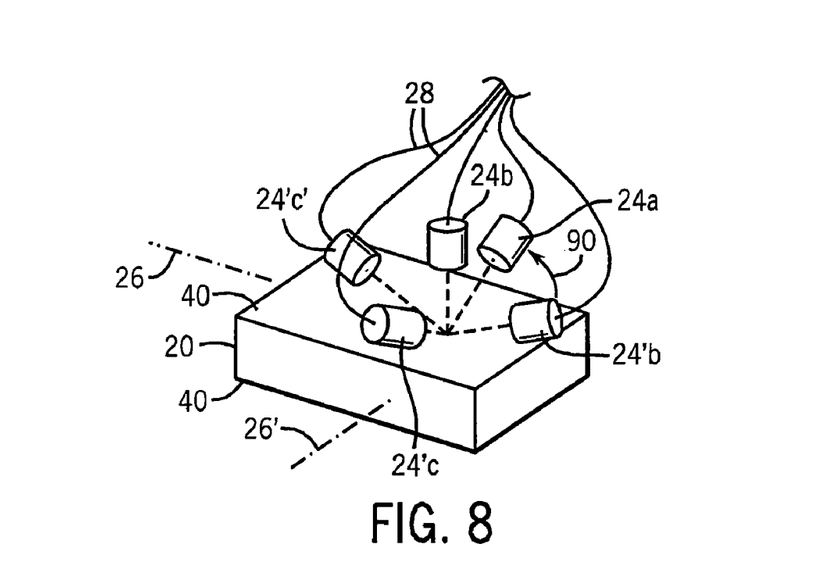
FIG. 8 is a diagram similar to that of FIG. 7 showing an alternative embodiment of the transducer array of FIG. 1 for evaluating two-dimensional or planar properties of materials.

Referring now to FIG. 8, the present invention is not limited to deducing axial properties along a single dimension, that is, along a single dimension generally perpendicular to the lateral access of the transducer array 18, but can be used to evaluate planar properties along axes at multiple angles generally perpendicular to the access direction of the transducer array 18.

In one embodiment, this may be done by establishing an array 18 of multiple oblique transducers 24a, 24'a, 24c and 24'c where transducers 24a and 24c are arranged as described above with respect to FIG. 1 to direct ultrasound within a vertical plane aligned with axis 26, and transducers 24'a and 24'c are arrayed similarly in a vertical plane but one that is generally perpendicular to the plane of transducers 24a and 24c and aligned with an axis 26' perpendicular to axis 26.

This approach will permit the collection of oblique information along two perpendicular axes 26 and 26' (with transducer 24b operating for both measurements to collect the perpendicular information), and by simple extension of the mathematics described above, to calculate axial properties in two dimensions within a plane of the material.

It will be understood that this approach can be extended by using additional oblique transducer pairs at more angles than the two perpendicular angles of axes 26 and 26' as shown in FIG. 8. Further it will be appreciated that a single transducer pair 24a and 24c can be rotated as indicated by arrow 90 about a perpendicular to the measured plane, while retaining their angles with respect to a planar surface of the material 20. Alternatively, or in addition, the multi-transducer array having transducers 24a, 24'a, 24c and 24'c may be rotated, for example by increments of less than 90 degrees, for even faster data acquisition.

Such a device as described above, may calculate planar stiffness in membranes like the pericardium, lung, heart valve leaflets, vocal folds, and fascia for compartment syndrome. The tissue 20 would need to be subject to loadings in multiple directions which may be accomplished by mechanical intervention or through the use of natural muscular motions by timing the measurements to take advantage of these periodic applied tensions.

It is specifically intended that the present invention not be limited to the embodiments and illustrations contained herein, but include modified forms of those embodiments including portions of the embodiments and combinations of elements of different embodiments as come within the scope of the following claims.

We claim:

1. An ultrasound system for measuring axial material properties of material using ultrasound, the ultrasound system comprising:
    an ultrasound transducer assembly providing at least one ultrasonic transducer for:
    (a) transmitting an ultrasound signal into the material along a first transverse direction perpendicular to an axial extent of the material and receiving the ultrasound signal after reflection and modification by the material to obtain a first and second echo signal from a first and second material location when the material is at a first and second tension applied along the axial extent of the material; and
    (b) transmitting an ultrasound signal into the material along a first oblique direction at an angle between the transverse direction and the axial extent of the material and receiving the ultrasound signal after reflection and modification by the material to obtain a first and second echo signal from the first and second material location when the material is at the first and second tension applied along the axial extent; and
    a processor receiving the first and second echo signal from the ultrasound signal along the transverse and oblique directions and processing the signals according to a stored program to determine at least one of axial stress and axial stiffness of the material.

2. The ultrasound system of claim 1 wherein the processor determines transverse material properties from the first and second echo signals from the ultrasonic signal along the transverse direction and determines axial properties from the transverse properties by analysis of a time of flight of the ultrasound along the transverse and oblique directions and a known geometry of a path of the ultrasound along the transverse and oblique directions.

3. The ultrasound system of claim 1 wherein the processor determines the transverse material properties from a time of flight of ultrasound between the first and second material positions and a reflection coefficient indicating reflected ultrasonic energy at the first and second material positions.

4. The ultrasound system of claim 3 where in the reflection coefficient is a measure of a relative power reflected at the material positions in a predetermined frequency range.

5. The ultrasound system of claim 1 wherein the processor determines axial stress in the material.

6. The ultrasound system of claim 1 wherein the processor determines axial stiffness of the material.

7. The ultrasound system of claim 1 wherein the ultrasonic transducer assembly includes three ultrasonic transducers fitting within a housing having surfaces to align the housing with respect to an axial direction of the material wherein the first ultrasonic transducer directs ultrasonic energy substantially perpendicular to the tissue when the housing is aligned with the tissue and the second and third ultrasonic transducers direct energy at complementary obtuse and acute angles with respect to a perpendicular to the axial direction when the housing is aligned with the axial direction.

8. The ultrasound system of claim 1 wherein the material is surrounded by a transmission material and the first and second material positions are interfaces between the material and the transmission material.

9. The ultrasound system of claim 8 wherein the transmission material is an elastomer of known material properties.

10. The ultrasound system of claim 1 wherein the material is selected from the group consisting of ligaments and tendons.

11. The ultrasound system of claim 1 wherein the ultrasound transducer assembly further provides at least one ultrasonic transducer for transmitting an ultrasound signal into the material along a second oblique direction at an angle between the transverse direction and a second axial extent of the material at an angle to the axial extent but within a plane with the axis extent perpendicular to the transverse direction, and receiving the ultrasound signal after reflection and modification by the material along the second oblique direction to obtain a first and second echo signal from the first and second material location when the material is at the first and second tension applied along the axial extent; and
    wherein the processor receives the first and second echo signal from the ultrasound signal along the transverse and oblique directions and processing the signals according to a stored program to determine at least one of planar stress and planar stiffness of the material.

12. A method of measuring axial material properties of material using ultrasound, the method comprising:
    using an ultrasound transducer assembly having at least one ultrasonic transducer to:
    (a) transmit an ultrasound signal into the material along a first transverse direction perpendicular to an axial extent of the material and receiving the ultrasound signal after reflection and modification by the material to obtain a first and second echo signal from a first and second material location when the material is at a first and second tension applied along the axial extent of the material; and
    (b) transmit an ultrasound signal into the material along a first oblique direction at an angle between the transverse direction and the axial extent of the material and receiving the ultrasound signal after reflection and modification by the material to obtain a first and second echo signal from the first and second material location when the material is at the first and second tension applied along the axial extent; and
    (c) using an electronic processor executing a program stored in a non-transient medium for processing the first and second echo signals from the ultrasound signal along the transverse and oblique directions to determine at least one of axial stress and axial stiffness of the material.

13. The method of claim 12 wherein the transverse material properties are determined from the first and second echo signals from the ultrasonic signal along the transverse direction and the axial properties are determined from the transverse properties by analysis of a time of flight of the ultrasound and along the transverse and oblique directions and a known geometry of a path of the ultrasound along the transverse and oblique direction.

14. The method of claim 12 wherein the transverse material properties are determined from a time of flight of ultrasound between the first and second material positions and a reflection coefficient indicating reflected ultrasonic energy at the first and second material positions.

15. The method of claim 14 where in the reflection coefficient is a measure of a relative power reflected at the material positions in a predetermined frequency range.

16. The method of claim 12 wherein axial stress in the material is determined.

17. The method of claim 12 wherein axial stiffness of the material is determined.

18. The method of claim 12 wherein the material is surrounded by a transmission material and the first and second material positions are interfaces between the material and the transmission material.

19. The method of claim 18 wherein the transmission material is an elastomer of known material properties.

20. The method of claim 12 wherein the material is selected from the group consisting of ligaments and tendons.

* * * * *